(12) United States Patent
Hasegawa

(10) Patent No.: US 7,062,014 B2
(45) Date of Patent: Jun. 13, 2006

(54) X-RAY ANALYZER FOR ANALYZING PLASTICS

(75) Inventor: Kiyoshi Hasegawa, Chiba (JP)

(73) Assignee: SII NanoTechnology Inc., Chiba (JP)

( * ) Notice: Subject to any disclaimer, the term of this patent is extended or adjusted under 35 U.S.C. 154(b) by 13 days.

(21) Appl. No.: 10/935,610

(22) Filed: Sep. 7, 2004

(65) Prior Publication Data

US 2005/0053193 A1    Mar. 10, 2005

(30) Foreign Application Priority Data

Sep. 4, 2003    (JP)    ............................. 2003-313085

(51) Int. Cl.
*G01T 1/36*    (2006.01)
(52) U.S. Cl. .......................................... 378/83; 378/88
(58) Field of Classification Search .................. 378/70, 378/71, 83, 86, 88, 57, 53
See application file for complete search history.

(56) References Cited

U.S. PATENT DOCUMENTS 5,115,459 A * 5/1992 Bertozzi ...................... 378/88
5,457,726 A * 10/1995 Miyazaki ...................... 378/45

* cited by examiner

*Primary Examiner*—David V. Bruce
*Assistant Examiner*—Hoon Song
(74) *Attorney, Agent, or Firm*—Adams & Wilks

(57) ABSTRACT

An object is to reduce the influence of chlorine in plastics when the metal concentrations in the plastics are analyzed. In an X-ray analyzer including an X-ray generating part for irradiating primary X-rays onto a sample and an X-ray detector for detecting an X-ray from the sample, primary X-rays is irradiated onto a plastic sample from the X-ray generating part, the X-ray intensity of chlorine is obtained from the plastic sample by the X-ray detector, and the scattered X-ray intensity where the primary X-ray has been scattered by the plastic sample is obtained by the X-ray detector. A chlorine X-ray intensity ratio calculating means for dividing the X-ray intensity of chlorine by the scattered X-ray intensity to calculate a chlorine X-ray intensity ratio is provided. The calculated chlorine X-ray intensity ratio and the chlorine concentration in the plastic sample have positive correlation each other. A relative chlorine concentration calculating means adapted to calculate the relative chlorine concentration in the plastic sample from the chlorine X-ray intensity ratio is provided.

7 Claims, 4 Drawing Sheets

X-RAY ANALYZER FOR ANALYZING PLASTICS

BACKGROUND OF THE INVENTION

1. Field of the Invention

The present invention relates to an X-ray analyzer which detects X-rays secondarily generated from a sample when X-rays are irradiated onto the sample and measures the metal concentrations in the sample.

2. Description of the Related Art

Traditionally, in the case where metal concentrations in a plastic are measured by an X-ray analyzer, when the type of this plastic is unknown, the metal concentrations are analyzed assuming that a typical plastic creates a calibration curve, where the horizontal axis is X-ray intensity and the vertical axis is metal concentrations. When a plastic discriminating device utilizing near-infrared rays and infrared rays can be used, metal concentrations in plastics are analyzed by a method in which information of polyvinyl chloride and polyethylene that are outputted from the plastic discriminating device are used to create calibration curves according to the types of plastics. As a method for determining types of plastics with near-infrared rays, a method is proposed in which near-infrared rays are irradiated onto a plastic product, the absorbance is measured in the range of 1000 to 2500 nm at pitches of a wavelength of six nanometers (hereinafter, it is expressed by 'nm'), differential values are calculated at individual measurement points and are separated into plus, zero or minus to know the characteristics of the absorbance, this plus/0/minus is compared with the data of plus/0/minus at each of known plastics measured beforehand, and the type of plastic is determined by the relevance factors between them (for example, see Patent Reference 1).

[Patent Reference 1] JP-A-6-308022 (PP. 3 to 4)

SUMMARY OF THE INVENTION

However, when the traditional method is used to determine a plastic and the determination results are used to analyze the metal concentrations in the plastic, a content of chlorine is wrongly determined and great errors sometimes occur in the concentration measurement. For example, in a plastic discriminating device utilizing near-infrared rays, when it measures a polyethylene containing chlorine, it simply outputs polyethylene as a determined result and it sometimes fails to determine the existence of chlorine. In the case where X-rays are used to measure metal concentrations in a plastic, when a great amount of chlorine is contained therein, the X-ray of a focused element is greatly absorbed by chlorine, and the resulting X-ray intensity of the focused element becomes small. When the X-ray intensity becomes small, the concentration that is smaller than the original concentration is outputted.

An object of the invention is to provide an X-ray analyzer which can properly determine a chlorine concentration and allows analysis in accordance with the chlorine concentration when metal concentrations in a plastic are analyzed.

The invention adopts the following means in order to solve the problem. More specifically, in an X-ray analyzer including an X-ray generating part for irradiating primary X-rays onto a plastic sample and an X-ray detector for detecting an X-ray from the plastic sample, primary X-rays is irradiated onto a plastic sample from the X-ray generating part, the X-ray intensity of chlorine is obtained from the plastic sample by the X-ray detector, and the scattered X-ray intensity where the primary X-ray has been scattered by the plastic is obtained by the X-ray detector. A chlorine X-ray intensity ratio calculating means for calculating a chlorine X-ray intensity ratio by dividing the X-ray intensity of chlorine by the scattered X-ray intensity is provided. The calculated chlorine X-ray intensity ratio and the chlorine concentration in the plastic sample have positive correlation each other, and the chlorine concentration in the plastic sample is calculated from the chlorine X-ray intensity ratio.

Furthermore, the X-ray analyzer includes a peak removing means adapted to remove a peak of a characteristic X-ray from the obtained X-ray spectrum when a signal of the characteristic X-ray exists in an energy area for calculating the scattered X-ray intensity, wherein the X-ray spectrum obtained from the peak removing means is used to calculate the scattered X-ray intensity.

The X-ray analyzer includes a standard substance data holding part in which a given plastic containing chlorine and a given plastic not containing chlorine are taken as standard substances and an X-ray intensity of chlorine and a scattered X-ray intensity thereof are stored as standard substance data, wherein the chlorine X-ray intensity ratio calculating means calculates chlorine X-ray intensity ratios for the two standard substances and an unknown sample, and the relative chlorine concentration calculating means calculates the relative chlorine concentration in the plastic sample from relationships among the three chlorine X-ray intensity ratios.

Moreover, a rigid polyvinyl chloride is used as a standard substance for the plastic containing chlorine in the standard substances, and the relative chlorine concentration in the plastic is calculated based on a chlorine content of this rigid polyvinyl chloride as a standard.

Besides, the X-ray analyzer includes a plurality of metal concentration calculating means (for example, calibration line) adapted to calculate metal concentrations in a plastic, wherein a correspondence table is created for associating the relative chlorine concentration with the metal concentration calculating means, and the plurality of the metal concentration calculating means are switched in accordance with the relative chlorine concentration in the plastic sample. Thus, the metal concentrations can be measured in accordance with the relative chlorine concentration, and errors can be reduced.

The X-ray analyzer includes a first metal concentration calculating means for calculating a concentration of a given metal in a plastic containing chlorine and a second metal concentration calculating means for calculating a concentration of the given metal in a plastic not containing chlorine among the plurality of the metal concentration calculating means, wherein the two metal concentration calculating means are used to calculate the metal concentrations in the plastics from X-ray intensities of the given metal obtained from the plastic samples separately, and the relative chlorine concentrations of the plastic samples and the metal concentrations calculated by the two calculating means are used to measure metal concentrations in accordance with the chlorine concentration in the plastic samples.

The invention has advantages described below.

Since the X-ray intensity of chlorine and the scattered X-ray intensity are increased and decreased nearly in proportion to the size of the plastic sample, the chlorine X-ray intensity ratio where the X-ray intensity of chlorine is divided by the scattered X-ray intensity is used to measure the chlorine concentration, and thus the chlorine concentration can be measured, which is hardly affected by the size of the sample.

Furthermore, the peak of the characteristic X-ray is removed from the obtained X-ray spectrum when the signal of the characteristic X-ray exists in the energy area for calculating the scattered X-ray intensity, and then the X-ray spectrum where the peak has been removed is used to calculate the scattered X-ray intensity. Accordingly, the chlorine concentration can be measured, which is hardly affected by metals contained in the plastic and metals attached on the plastic surface.

Moreover, the plastic containing chlorine and the plastic not containing chlorine are used as the standard substances for discriminating plastics to measure at each means, and thus the chlorine concentration where the individual differences of the X-ray analyzers are eliminated can be measured.

Besides, a rigid polyvinyl chloride is used as a standard substance for the plastic containing chlorine, and thus chlorine concentration information can be outputted based on a chlorine content of the rigid polyvinyl chloride.

Additionally, the measurement result of the chlorine content is used to switch the metal concentration calculating means, and thus the metal concentration can be measured in accordance with the chlorine concentration.

Furthermore, the metal concentration calculating means for calculating the metal concentrations in the plastic containing chlorine and the metal concentration calculating means for calculating the metal concentrations in the plastic not containing chlorine are provided, the metal concentrations in the plastics are calculated by the two metal concentration calculating means separately, and the chlorine content and the metal concentrations calculated by the two calculating means are used. Accordingly, the metal concentration can be measured in accordance with the chlorine concentration.

BRIEF DESCRIPTION OF THE DRAWINGS

The teachings of the invention can be readily understood by considering the following detailed description in conjunction with the accompanying drawings, in which.

DESCRIPTION OF THE PREFERRED EMBODIMENT

Hereinafter, an embodiment according to the invention will be described with reference to the drawings.

Figure 1:
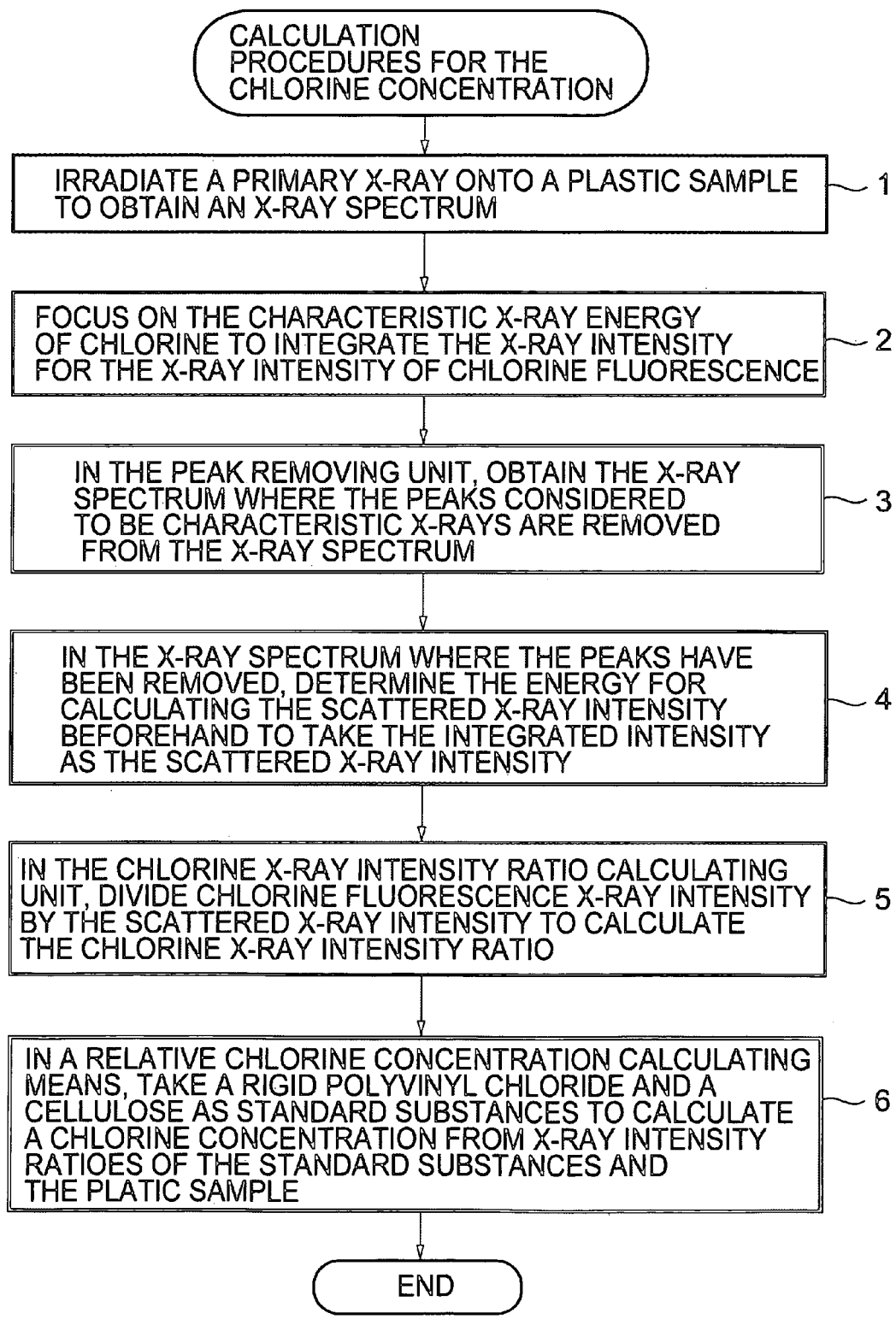
FIG. 1 is procedures for implementing the invention.
Figure 2:
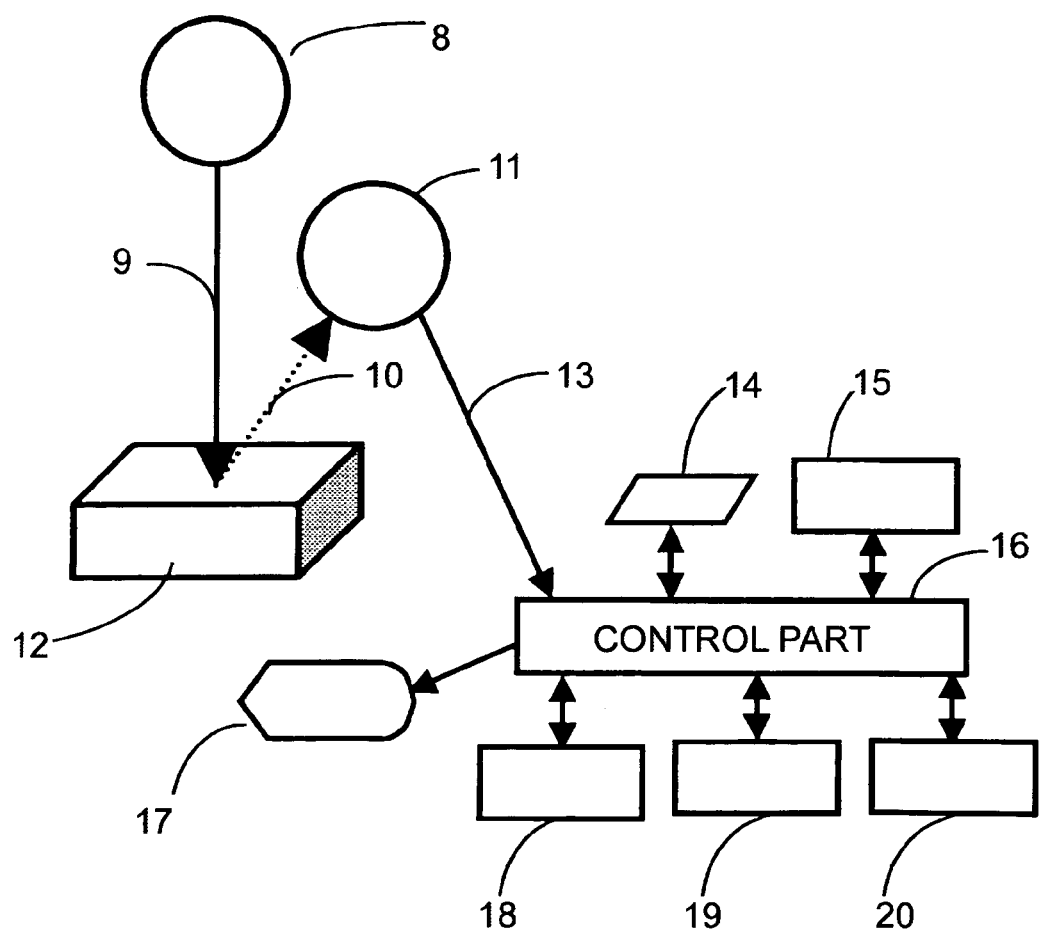
FIG. 2 is an exemplary device configuration for implementing the invention.

FIG. 1 describes calculation procedures for the relative chlorine concentration in a plastic sample. FIG. 2 is an exemplary device configuration for implementing the invention.

At step 1, primary X-rays 9 is irradiated onto a plastic sample 12 to obtain an X-ray spectrum 13. An X-ray tube 8 is used as an example of an X-ray generating means, and a Si—Li detector 11 is used as an example of an X-ray detector. 17 denotes a display unit. Since chlorine contents of rigid polyvinyl chloride and plasticized polyvinyl chloride are significantly great, chlorine contents in plastics can be measured for about ten seconds to obtain a sufficient signal amount.

At step 2, the characteristic x-ray energy of chlorine is focused to integrate the X-ray intensity for calculating the X-ray intensity of chlorine. Kα-ray of chlorine is used as an example of the characteristic X-ray energy of chlorine, and the X-ray intensity is integrated in the energy area of 2.48 to 2.76 (keV). The X-ray intensities of chlorine in Table 1 are obtained from a rigid polyvinyl chloride, a plasticized polyvinyl chloride, and a polyethylene individually. The X-ray intensity of chlorine was 0 (CPS) in the polyethylene not containing chlorine, and the X-ray intensity of chlorine was 2612 (GPS) in the rigid polyvinyl chloride.

TABLE 1

| Sample Type | X-ray Intensity of Chlorine (CPS) |
| --- | --- |
| Rigid Polyvinyl Chloride | 2612 |
| Plasticized Polyvinyl Chloride | 2200 |
| Polyethylene | 0 |

Figure 3:
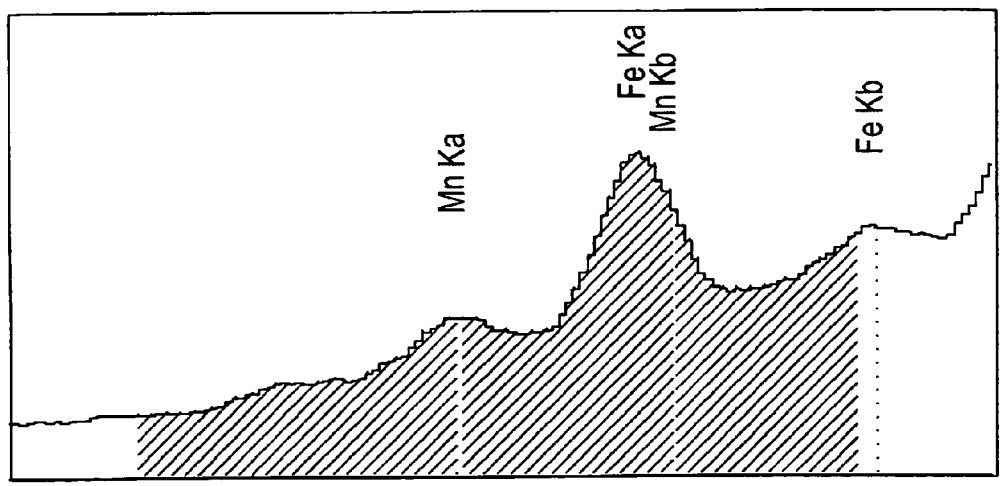
FIG. 3 is an X-ray spectrum before characteristic X-rays are removed.

At step 3, the peaks considered to be characteristic X-rays are removed from the X-ray spectrum obtained at step 1 by a peak removing means 18. FIG. 3 shows the X-ray spectrum before the characteristic X-rays are removed. In this example, the characteristic X-rays of iron and manganese are confirmed. The peak removing means 18 filters and removes the peaks of the characteristic X-rays to obtain the X-ray spectrum shown in FIG. 4 where the peaks have been removed.

Figure 4:
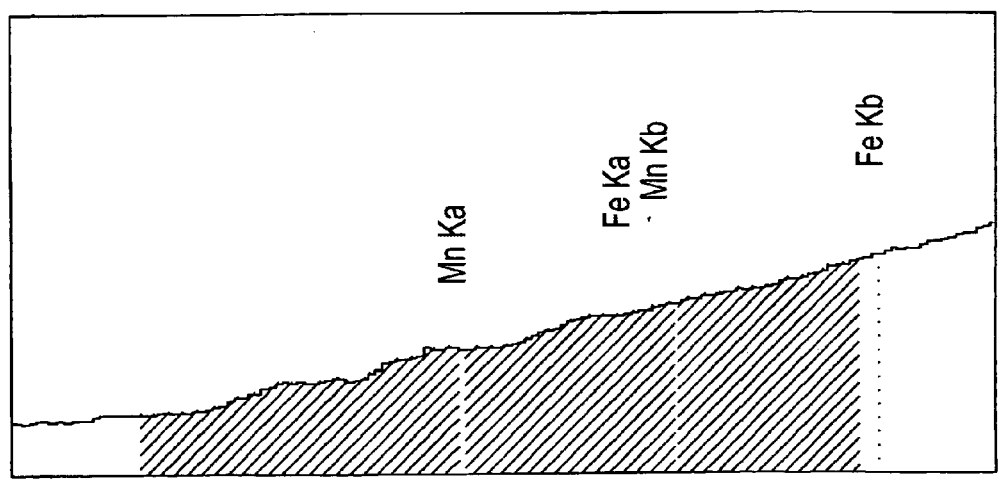
FIG. 4 is the X-ray spectrum after the characteristic X-rays are removed.

At step 4, in the X-ray spectrum where the peaks of the characteristic X-rays have been removed, the energy for calculating the scattered X-ray intensity is determined beforehand and the integrated intensity is to be the scattered X-ray intensity. The hatched areas in FIGS. 3 and 4 are examples of calculating the scattered X-ray intensity in the energy area of 5 to 7 (keV). The X-ray intensity of Kα-ray of chlorine is not varied when the thickness of the plastic exceeds 0.5 mm even though the thickness of the plastic is varied. On this account, when the thickness of the plastic exceeds 0.5 mm and the material is uniform, the X-ray of Kα-ray of chlorine is not varied greatly at the time when the sample thickness is varied. Table 2 shows the measurement results that a rigid polyvinyl chloride was taken as an example and the thickness was varied. The thickness here is the sample thickness seen from the direction of the detector. The integrated intensity of Kα-ray is used for the X-ray fluorescence intensity of chlorine, and the integrated intensity of 5 to 7 (keV) is used for the scattered X-ray intensity.

When the sample thickness is equal to or below 0.5 mm, the X-ray fluorescence intensity of chlorine is suddenly dropped. When the sample thickness exceeds 0.5 mm, the X-ray fluorescence intensity of chlorine and the scattered X-ray intensity are not varied so much, and thus it can be determined that it is fine to calculate the scattered X-ray in the energy area of 5 to 7 (keV).

At step 5, the X-ray intensity of chlorine is divided by the scattered X-ray intensity to calculate the X-ray intensity ratio. This is conducted by a chlorine X-ray intensity ratio calculating means 15. The reason why the X-ray intensity ratio is used is that the X-ray intensity varied by the sample size is divided by the scattered X-ray intensity to normalize it and then the chlorine concentration can be measured based on a constant criterion all the time regardless of the sample size. Tables 2 and 3 show the measurements of rigid polyvinyl chlorides. Table 2 is data when the sample thickness was varied, and Table 3 is data when the sample area seen from the detector was varied. It is revealed that the X-ray intensity ratio is uniform in these examples. In the case where the X-ray intensity of chlorine is simply used, the X-ray intensity of chlorine is increased and decreased when the sample area is varied.

At step 6, a relative chlorine concentration calculating means 19 is used to calculate a chlorine content of an unknown sample, where a rigid polyvinyl chloride and a cellulose are taken as standard substances.

TABLE 2

| Sample Thickness (mm) | X-ray Intensity of Chlorine (CPS) | Scattered X-ray Intensity (CPS) | X-ray Intensity Ratio |
|---|---|---|---|
| 0.5 | 2669 | 134 | 19.9 |
| 1.0 | 2861 | 130 | 22.0 |
| 2.0 | 2878 | 124 | 23.2 |
| 5.0 | 2881 | 132 | 21.8 |
| 10.0 | 2871 | 137 | 20.9 |

TABLE 3

| Sample Area (mm$^2$) | X-ray Intensity of Chlorine (CPS) | Scattered X-ray Intensity (CPS) | X-ray Intensity Ratio |
|---|---|---|---|
| 8 | 583 | 30 | 19.4 |
| 16 | 1190 | 59 | 20.2 |
| 40 | 2820 | 140 | 20.1 |

The calculation equation is (the unknown sample intensity ratio–the cellulose intensity ratio)÷(the rigid polyvinyl chloride intensity ratio–the cellulose intensity ratio)×100; hereinafter it is denoted by PVC % in the specification. PCV % is the indicator for expressing the relative chlorine concentration based on a rigid polyvinyl chloride, and it is adopted for facilitating the calculation process when the metal concentrations are calculated, which will be described later. The cellulose intensity ratio or the rigid polyvinyl chloride intensity ratio is inputted into control section 16 as a standard substance data 14.

The unknown sample intensity ratio is that an unknown sample is measured and the X-ray intensity of chlorine is divided by the scattered X-ray intensity. The cellulose intensity ratio is that a cellulose is measured and the X-ray intensity of chlorine is divided by the scattered X-ray intensity. The rigid polyvinyl chloride intensity ratio is that a rigid polyvinyl chloride is measured and the X-ray of chlorine intensity is divided by the scattered X-ray intensity. The reason why the cellulose intensity ratio is used for subtraction is that when the X-ray intensity ratio of cellulose with a chlorine concentration of 0% does not become zero because of the reason of X-ray measurement, the numeric value at that time is considered to be an offset and the offset is removed to calculate PVC %.

The description above is the procedures for measuring the relative chlorine concentration in plastics.

Next, the mechanism will be described that the calculation result of the relative chlorine concentration in a plastic is tied to the metal analysis in the plastic.

A first method is the method of selecting the conditions for analysis in accordance with the levels of the relative chlorine concentration. This will be described.

Figure 5:
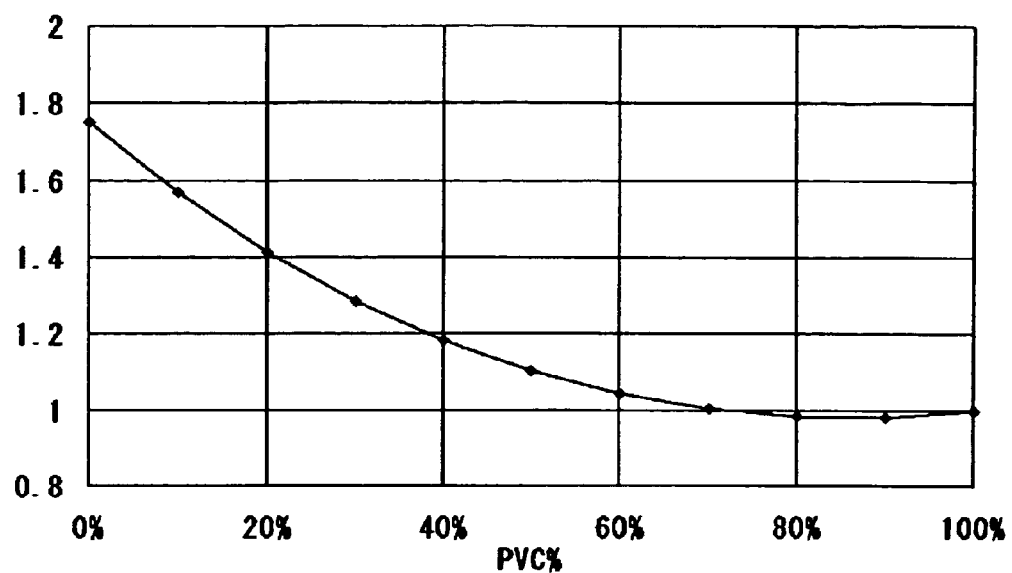
FIG. 5 is the variation of the calculated concentrations when plastics having different chlorine contents are analyzed in a calibration curve for analyzing lead contained in a rigid polyvinyl chloride.

The analysis error when the relative chlorine concentration is varied is depicted as a graph shown in FIG. 5. FIG. 5 is a graph illustrating the analysis error in the case where a calibration curve method is used when lead contained in a rigid polyvinyl chloride is analyzed. In the graph, the value of the longitudinal axis is 1 when PVC % is 100%.

This shows the following. A calibration curve is first created which shows the relationship between the X-ray intensity and the lead concentration when PVC is 100%. When this calibration curve is used with respect to a plastic with lower PVC %, the lead concentration is excessively calibrated. More specifically, it shows that the ratio of absorption of the characteristic X-ray of lead is decreased by chlorine to calculate the lead concentration higher. The event that the value of the longitudinal axis is increased when PVC % is close to 0% means that the lead concentration is outputted higher than the original value. For example, the concentration 1.75 times the original lead concentration is wrongly outputted when PVC % is zero.

This error is not acceptable. Therefore, a table is created for switching metal concentration calculating means in accordance with PVC % as Table 4, and the X-ray analyzer automatically selects the metal concentration calculating means 20 to decrease the analysis error due to the variation in the chlorine concentration. More specifically, in the calibration curve method, a calibration curve for use is switched in accordance with the chlorine concentration in a plurality of the calibration curves.

TABLE 4

| PVC % | Metal Concentration Calculating Means |
|---|---|
| 0 to 10 | For 0% of PVC % |
| 11 to 50 | For 30% of PVC % |
| 51 to 90 | For 70% of PVC % |
| 91 to 100 | For 100% of PVC % |

A second method is the method that includes a first metal concentration calculating means adapted to calculate a concentration of a given metal in a plastic containing chlorine and a second metal concentration calculating means adapted to calculate a concentration of the given metal in a plastic not containing chlorine among the plurality of the metal concentration calculating means, wherein the two metal concentration calculating means are used to calculate the metal concentrations in the plastics from X-ray intensities of the given metal obtained from the plastic samples, and the relative chlorine concentrations of the plastic samples and the metal concentrations calculated by the two calculating means are used to measure metal concentrations in accordance with the chlorine concentrations in the plastic samples. For the plastic containing chlorine, plastics containing chlorine of 50 wt. % or greater are fine; for example, rigid polyvinyl chlorides are used.

As means for calculating the metal concentrations in the plastic containing chlorine, the standard substance of a rigid polyvinyl chloride is prepared to create the calibration curve for lead analysis. As means for calculating the metal concentrations in the plastic not containing chlorine, the standard substance of a cellulose is prepared to create the calibration curve for lead analysis.

As a method for creating the calibration curve, there are methods that the lead concentration is used for the vertical axis and the lead X-ray intensity is used for the horizontal axis and that the X-ray intensity ratio is used the same as when the chlorine concentration is calculated. When samples with a uniform size are measured, the lead X-ray intensity is used for the horizontal axis to calculate the lead concentration. However, when the sample size is varied at every time of measurement, it is fine to adopt the lead X-ray intensity ratio where the lead X-ray intensity is divided by the scattered X-ray intensity for the horizontal axis. Then, as a method for calculating a chlorine content, PVC % is utilized based on rigid polyvinyl chloride. When the concentration obtained from the use of the calibration curve for the plastic containing chlorine with respect to the X-ray intensity or the X-ray intensity ratio of certain lead is named as the PVC lead concentration, and the concentration obtained from the calibration curve for the plastic not containing chlorine is named as the non-PVC lead concentration, the final lead concentration is calculated by the PVC lead concentration×PVC %÷100+the non-PVC lead concentration×(1−(PVC %÷100)). In other wards, the metal concentrations calculated by the two calibration curves are weighed with PVC % to calculate the final metal concentrations.

Figure 6:
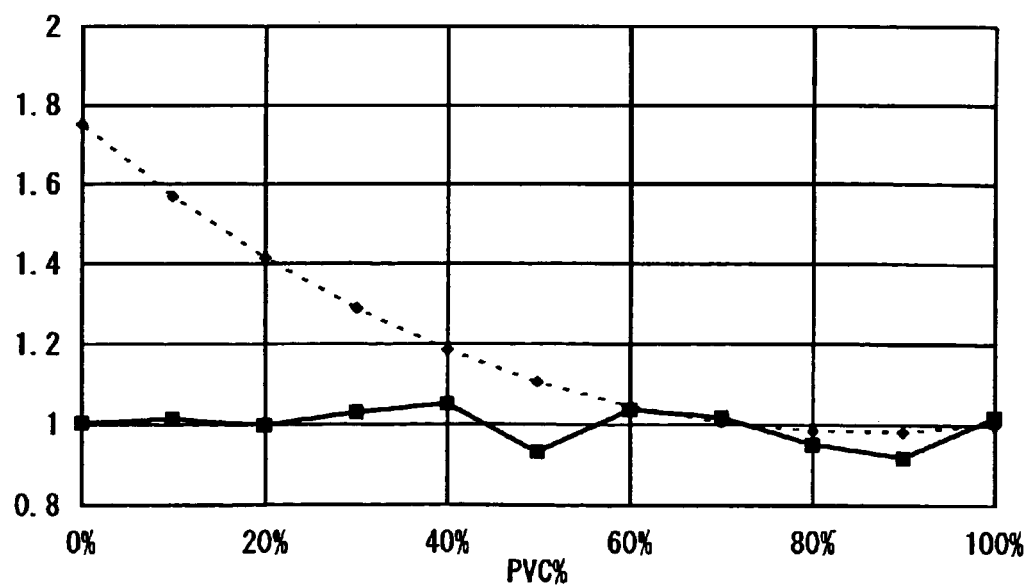
FIG. 6 is the variation of the calculated concentrations when lead is analyzed in plastics having different chlorine contents after the invention is adopted; a solid line shows data after adopted.

When the lead concentration in a plastic was measured by the method according to the invention, the analysis error depicted in the graph shown in FIG. 5 could be shrunken as data of a solid line shown in FIG. 6, and the maximum error of the lead concentration was allowed to be relatively 10% or below. FIG. 6 includes the statistical fluctuation error of X-rays because it contains actual measurement data.

Although there is a method for creating the calibration curve to correct matrix effects of chlorine with the use of an orthogonal table when the calibration curve is created, the number of standard substances is significantly increased when the number of metals for analysis is grown, and thus the operations become difficult. In order to solve the problem, the invention is proposed.

What is claimed is:

1. An X-ray analyzer comprising:
   an X-ray generator for irradiating primary X-rays onto a plastic sample; and
   an X-ray detector for detecting X-rays from the plastic sample, the X-ray analyzer further comprising:
   means for separating an X-ray intensity of chlorine and a scattered X-ray intensity from an X-ray intensity obtained by the X-ray detector;
   a chlorine X-ray intensity ratio calculating means for calculating a chlorine X-ray intensity ratio by dividing the separated X-ray intensity of chlorine by the separated scattered X-ray intensity; and
   a relative chlorine concentration calculating means for calculating a chlorine concentration in the plastic sample from comparison of the calculated chlorine X-ray intensity ratio with a chlorine X-ray intensity ratio of a plastic reference sample having a known predetermined chlorine concentration.

2. The X-ray analyzer according to claim 1, wherein the separating means includes a peak removing means for removing a peak of a characteristic X-ray from the obtained scattered X-ray spectrum when a signal of the characteristic X-ray exists in an energy area used to calculate the scattered x-ray intensity,
wherein the X-ray spectrum obtained from the peak removing means is used to calculate the scattered X-ray intensity.

3. The X-ray analyzer according to claim 1 further comprising a standard substance data holder in which a given plastic containing chlorine and a given plastic not containing chlorine are taken as standard substances and an X-ray intensity of chlorine and a scattered X-ray intensity thereof are stored as standard substance data,
   wherein the chlorine X-ray intensity ratio calculating means calculates chlorine X-ray intensity ratios for the two standard substances and the plastic sample, and
   the relative chlorine concentration calculating means calculates the relative chlorine concentration in the plastic sample from relationships among the three calculated chlorine X-ray intensity ratios.

4. The X-ray analyzer according to claim 3, wherein the plastic containing chlorine is a rigid polyvinyl chloride.

5. The X-ray analyzer according to claim 1 further comprising a plurality of metal concentration calculating means for calculating metal concentrations in the plastic sample,
   wherein a correspondence table is created for associating the relative chlorine concentration with the metal concentration calculating means, and
   any one of the plurality of the metal concentration calculating means is switched in accordance with the relative chlorine concentration in the plastic sample to measure metal concentrations.

6. The X-ray analyzer according to claim 5 further comprising:
   a first metal concentration calculating means for calculating a concentration of a given metal in a plastic containing chlorine and a second metal concentration calculating means for calculating a concentration of the given metal in a plastic not containing chlorine among the plurality of the metal concentration calculating means,
   wherein the two metal concentration calculating means are used to calculate the metal concentrations in the plastic using X-ray intensity of the given metal obtained from the plastic sample respectively, and
   the chlorine concentrations of the plastic sample and the metal concentrations calculated by the two calculating means are used to measure a metal concentration in accordance with the chlorine concentration in the plastic samples.

7. An X-ray analyzer comprising:
   an X-ray generator for irradiating primary X-rays onto a plastic sample; and
   an X-ray detector for detecting X-rays from the plastic sample, the X-ray analyzer further comprising:
   means for separating an X-ray intensity of chlorine and a scattered X-ray intensity from an X-ray intensity obtained by the X-ray detector; and
   a chlorine X-ray intensity ratio calculating means for calculating a chlorine X-ray intensity ratio by dividing the separated X-ray intensity of chlorine by the separated scattered X-ray intensity.

* * * * *